(12) United States Patent  (10) Patent No.: US 7,459,645 B2
Skinner et al.  (45) Date of Patent: Dec. 2, 2008

(54) SEAT FORCE SENSOR FOR A PATIENT SUPPORT

(75) Inventors: Andrew F. Skinner, Batesville, IN (US); James R. Stolpmann, Bakersville, NC (US); Terry L. Richter, Carmel, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 10/581,870

(22) PCT Filed: Dec. 10, 2004

(86) PCT No.: PCT/US2004/041358

§ 371 (c)(1),
(2), (4) Date: Apr. 12, 2007

(87) PCT Pub. No.: WO2005/059486

PCT Pub. Date: Jun. 30, 2005

(65) Prior Publication Data

US 2007/0272450 A1  Nov. 29, 2007

Related U.S. Application Data

(60) Provisional application No. 60/529,198, filed on Dec. 12, 2003.

(51) Int. Cl.
 *G01G 19/52* (2006.01)
 *A47C 27/10* (2006.01)
(52) U.S. Cl. .................. 177/144; 177/254; 5/713
(58) Field of Classification Search ........... 177/144, 177/208–209, 254; 5/713
See application file for complete search history.

(56) References Cited

U.S. PATENT DOCUMENTS

| 4,926,951 A | 5/1990 | Carruth et al. |
| 4,934,468 A | 6/1990 | Koerber, Sr. et al. |
| 4,953,244 A | 9/1990 | Koerber, Sr. et al. |
| 4,961,470 A | 10/1990 | Koerber, Sr. et al. |
| 4,974,692 A | 12/1990 | Carruth et al. |
| 5,148,706 A * | 9/1992 | Masuda et al. ............. 73/172 |
| 5,173,977 A | 12/1992 | Carruth et al. |
| 5,393,935 A | 2/1995 | Hasty et al. |
| 5,672,849 A | 9/1997 | Foster et al. |
| 5,780,781 A * | 7/1998 | Berger et al. ............ 177/126 |
| 5,808,552 A | 9/1998 | Wiley et al. |
| 5,859,390 A | 1/1999 | Stafford et al. |
| 6,045,155 A * | 4/2000 | Cech et al. .............. 280/735 |
| 6,058,341 A * | 5/2000 | Myers et al. ............. 701/45 |
| 6,067,019 A | 5/2000 | Scott |

(Continued)

FOREIGN PATENT DOCUMENTS

JP  2007-054606  *  4/2007

(Continued)

OTHER PUBLICATIONS

Written Opinion of the International Searching Authority dated Jun. 22, 2006 issued by the European Patent Office.

*Primary Examiner*—Randy W Gibson
(74) *Attorney, Agent, or Firm*—Barnes & Thornburg LLP

(57) ABSTRACT

A weighing system associated with a mattress and configured to measure a patient's weight while the patient is positioned on the mattress.

20 Claims, 19 Drawing Sheets

U.S. PATENT DOCUMENTS

| | | | |
|---|---|---|---|
| 6,094,762 A * | 8/2000 | Viard et al. | 5/713 |
| 6,133,837 A | 10/2000 | Riley | |
| 6,208,250 B1 | 3/2001 | Dixon et al. | |
| 6,252,512 B1 | 6/2001 | Riley | |
| 6,438,776 B2 | 8/2002 | Ferrand et al. | |
| 6,490,936 B1 * | 12/2002 | Fortune et al. | 73/862.581 |
| 6,649,848 B2 * | 11/2003 | Kriger | 177/25.13 |
| 6,680,443 B2 | 1/2004 | Dixon | |
| 6,721,980 B1 | 4/2004 | Price et al. | |
| 6,791,460 B2 | 9/2004 | Dixon et al. | |
| 6,818,842 B2 * | 11/2004 | Gray et al. | 177/144 |
| 6,819,254 B2 | 11/2004 | Riley | |
| 7,199,311 B1 * | 4/2007 | Buckner et al. | 177/144 |
| 7,219,380 B2 * | 5/2007 | Beck et al. | 5/713 |
| 2005/0076715 A1 * | 4/2005 | Kuklis et al. | 73/541 |
| 2006/0236464 A1 * | 10/2006 | Beck et al. | 5/713 |
| 2007/0008156 A1 * | 1/2007 | Ueda et al. | 340/575 |
| 2007/0276202 A1 * | 11/2007 | Raisanen et al. | 600/301 |
| 2008/0097250 A1 * | 4/2008 | Tochigi et al. | 600/595 |

FOREIGN PATENT DOCUMENTS

| | | |
|---|---|---|
| WO | WO0024353 A | 5/2000 |
| WO | WO03/024380 A | 3/2003 |

* cited by examiner

SEAT FORCE SENSOR FOR A PATIENT SUPPORT

CROSS-REFERENCE TO RELATED APPLICATION

This application is the U.S. national phase under 35 U.S.C. § 371 of PCT International Application No. PCT/US2004/041358, which has an international filing date of Dec. 10, 2004, designating the United States of America, and claims the benefit of U.S. Provisional Patent Application No. 60/529,198, which was filed Dec. 12, 2003. The disclosures of each of these prior applications are hereby incorporated by reference herein.

BACKGROUND AND SUMMARY OF THE INVENTION

The present invention relates to a weighing system for sensing a patient's weight when the patient is positioned on a patient support such as a hospital bed.

Some patients may be confined to a bed for extended periods of time making it difficult to weigh the patient on conventional weighing scales. Other patients may be wholly or partially disabled and unable to be positioned on a conventional weighing scale. The present invention provides a weighing system which can be added to or incorporated into a mattress and has the ability to accurately measure a patient's weight while the patient is positioned on the patient support. The weighing system can also provide the patient weight data to other systems, such as an air pressure controller for an inflatable mattress supporting the patient.

DETAILED DESCRIPTION OF THE DRAWINGS

Figure 1:
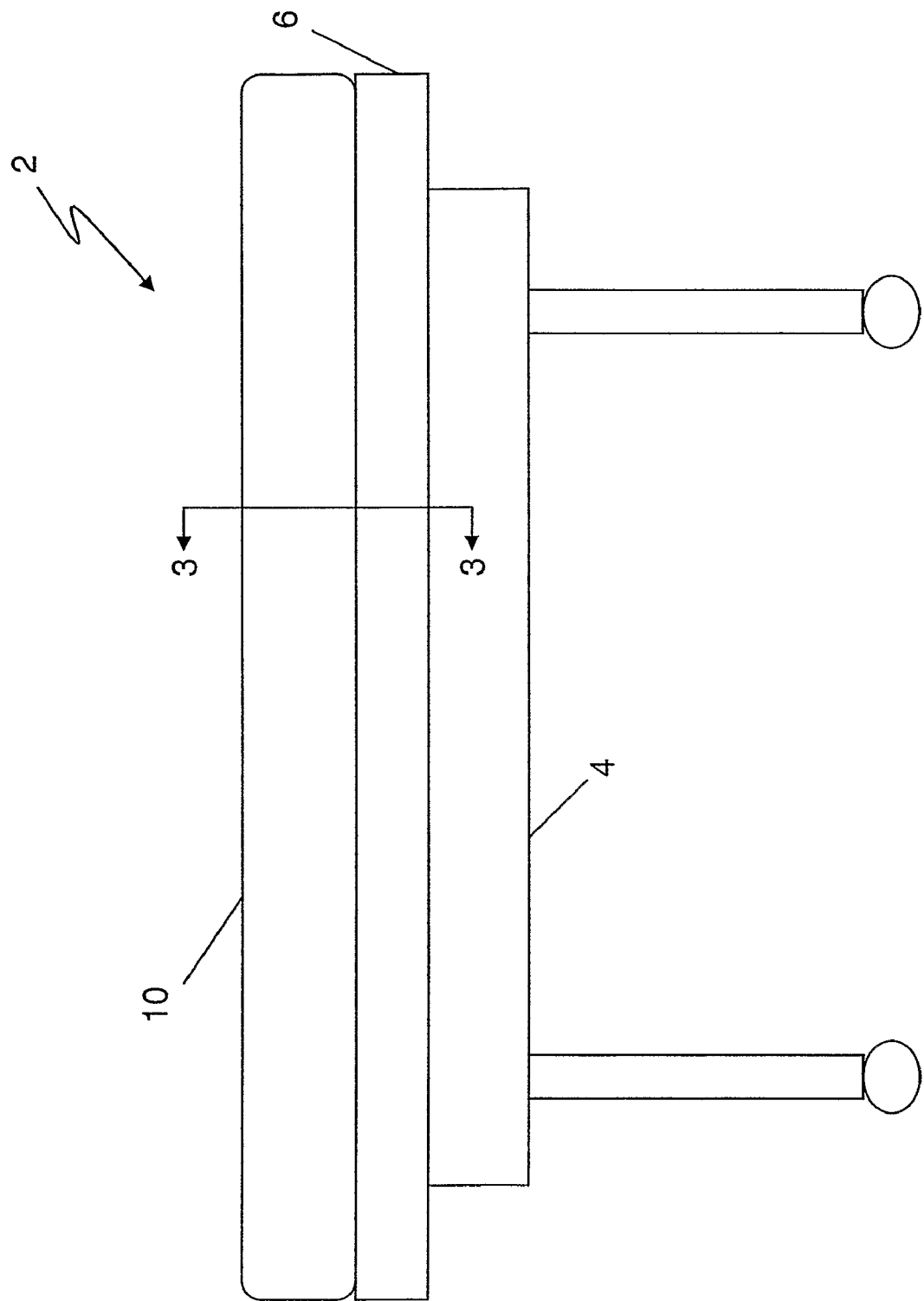
FIG. 1 is a side elevational view, in partial schematic, of a patient support.
Figure 2:
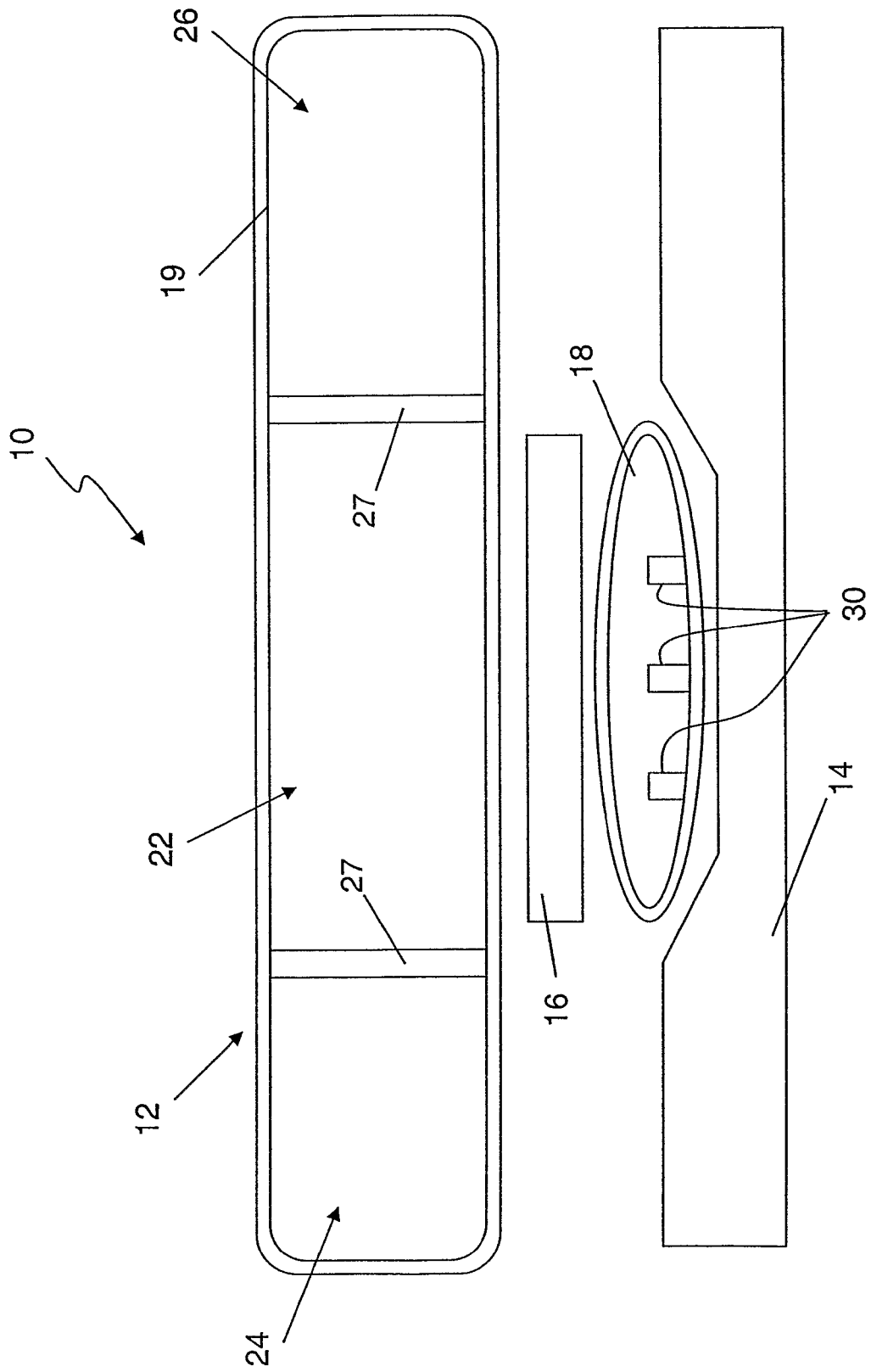
FIG. 2 is a partially exploded side elevational view, in partial schematic, of an illustrative embodiment of a mattress assembly in accordance with the present invention.

Referring to FIG. 1, a patient support 2 including a frame 4, a deck 6, and an illustrative mattress assembly 10 is shown. The mattress assembly 10 may be utilized in connection with any type of conventional patient support 2, such as a hospital bed, a stretcher, etc. Referring now to FIG. 2, mattress assembly 10 illustratively includes a fluid mattress or support 12, a collector plate 16, a seat force sensor 18, and a base support 14. In various embodiments, fluid mattress 12 and base support 14 include air bladders, foam sections or any other suitable form of mattress material. In one illustrative embodiment, fluid mattress 12 includes at least one inflatable air bladder 19 having a head section 26, a seat section 22, and a foot section 24. In certain embodiments, the head section 26, seat section 22, and foot section 24 are fluidly separated by walls 27. In one illustrative embodiment, base support 14 includes a hard foam material, while fluid mattress 12 includes a plurality of air bladders 19 such as those described in U.S. Pat. Nos. 6,295,657 and 6,584,528, the disclosures of which are expressly incorporated by reference herein. In another illustrative embodiment, mattress 12 and base support 14 both comprise a foam material. In a further embodiment, the air bladders 19 of the mattress 12 include foam material.

As shown in FIG. 2, collector plate 16 is illustratively positioned above seat force sensor 18 and under the seat section 22 of fluid mattress 12. Collector plate 16 is configured to substantially support a patient's entire seat region to substantially direct, focus and/or uniformly apply the patient's weight to seat force sensor 18. Collector plate 16 is illustratively made of metal, plastic, wood, foam, or any other suitable rigid or semi-rigid material. The collector plate 16 could also comprise an inflated air bladder. In one illustrative embodiment, seat force sensor 18 is a single air bladder placed under collector plate 16. Seat force sensor 18 can be any form of conventional air bladder, and its dimensions are sufficiently long and wide enough so that the patient's sacral or seat region substantially covers the bladder area. Seat force sensor 18 may also include internal baffles 30 so it is able to maintain a predictable shape and volume as internal pressure increases. The air bladder thickness of the seat force sensor 18 is sufficiently thin so that the inflation of the air bladder will not be an annoyance to a patient positioned thereabove.

Figure 3:
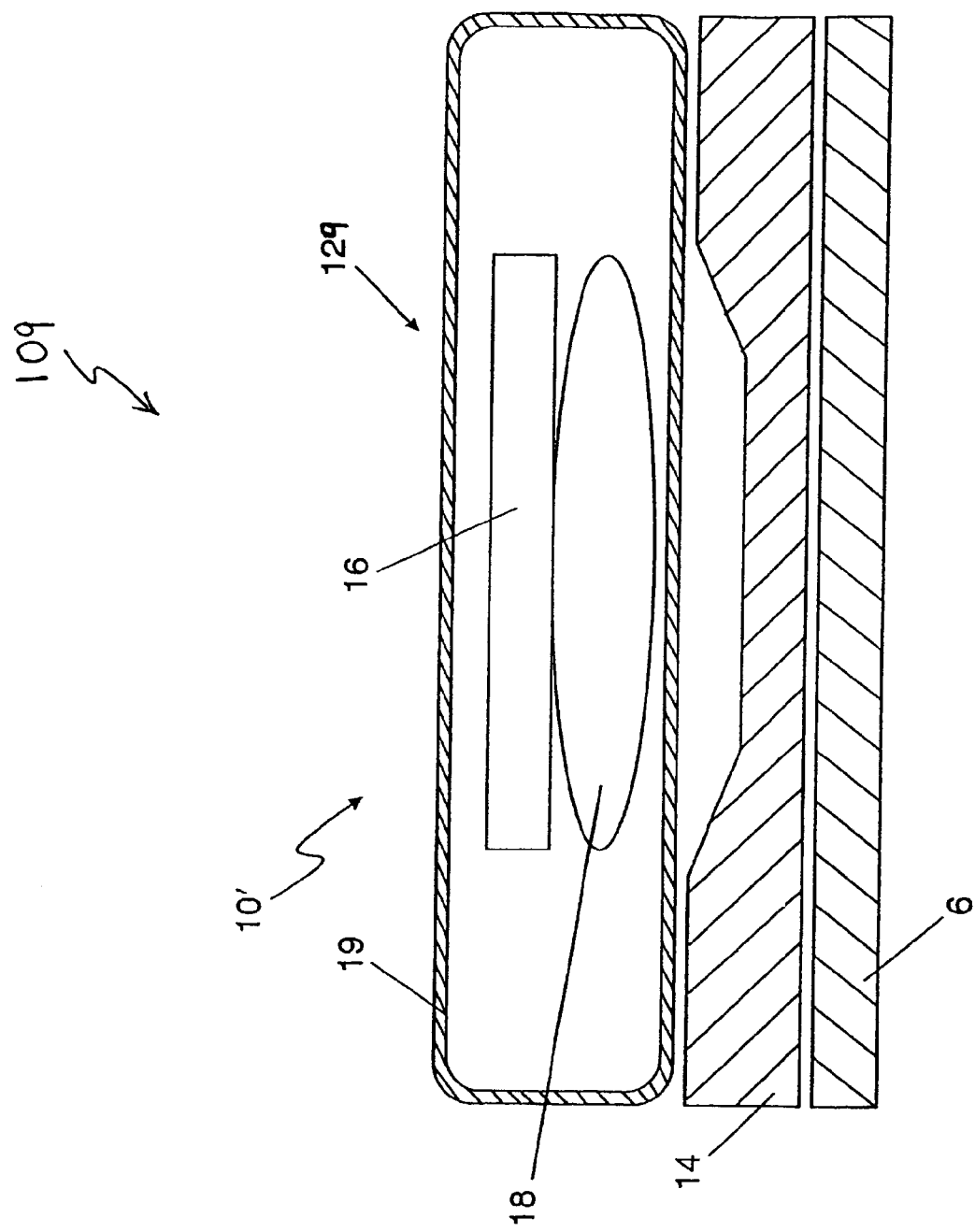
FIG. 3 is a cross-sectional view, in partial schematic, taken along line 3-3 of FIG. 1 of another embodiment of a mattress assembly.

Referring now to FIG. 3, a further illustrative mattress assembly 109, including seat force sensor 18, is shown. Fluid mattress or support 129 is shown positioned on base support 14 of mattress assembly 109. Mattress assembly 109 is supported by deck 6 of patient support 2. In this embodiment, fluid mattress 129 of the mattress assembly 109 includes one or more air bladders 19. Seat force sensor 18 and collector plate 16 are positioned within air bladder 19 of fluid mattress 129. More particularly, seat force sensor 18 and collector plate 16 are positioned below the patient's sacral or seat region while positioned within air bladder 19 of fluid mattress 129. In another illustrative embodiment, seat force sensor 18 is used without a collector plate 16.

Figure 4:
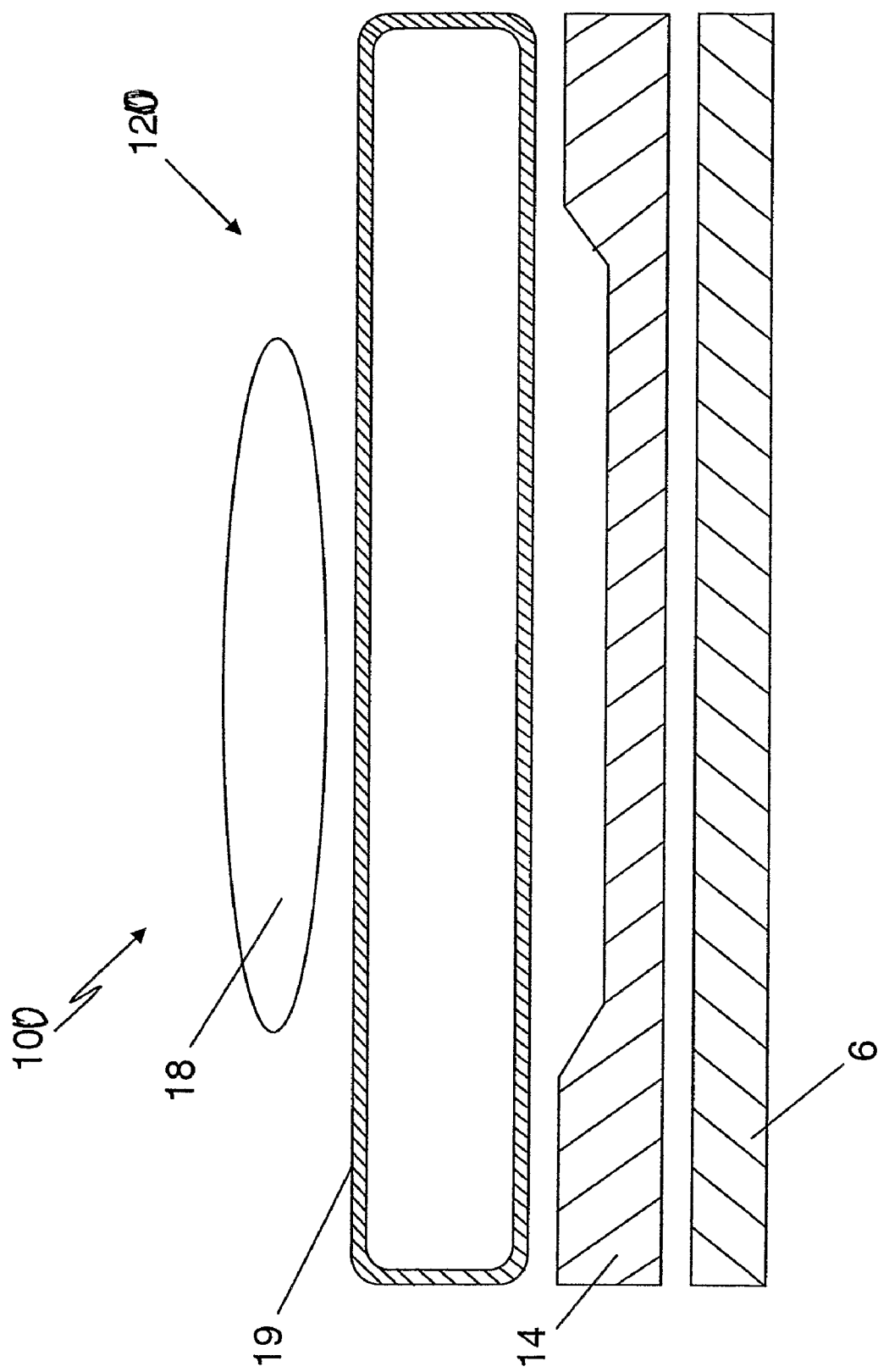
FIG. 4 is a cross-sectional view, in partial schematic, similar to FIG. 3, of another embodiment of a mattress assembly.

In another alternative embodiment of mattress assembly 100, as shown in FIG. 4, seat force sensor 18 is positioned on top of fluid mattress 120. In this position, seat force sensor 18 is directly beneath a patient positioned on mattress assembly 100.

Figure 5:
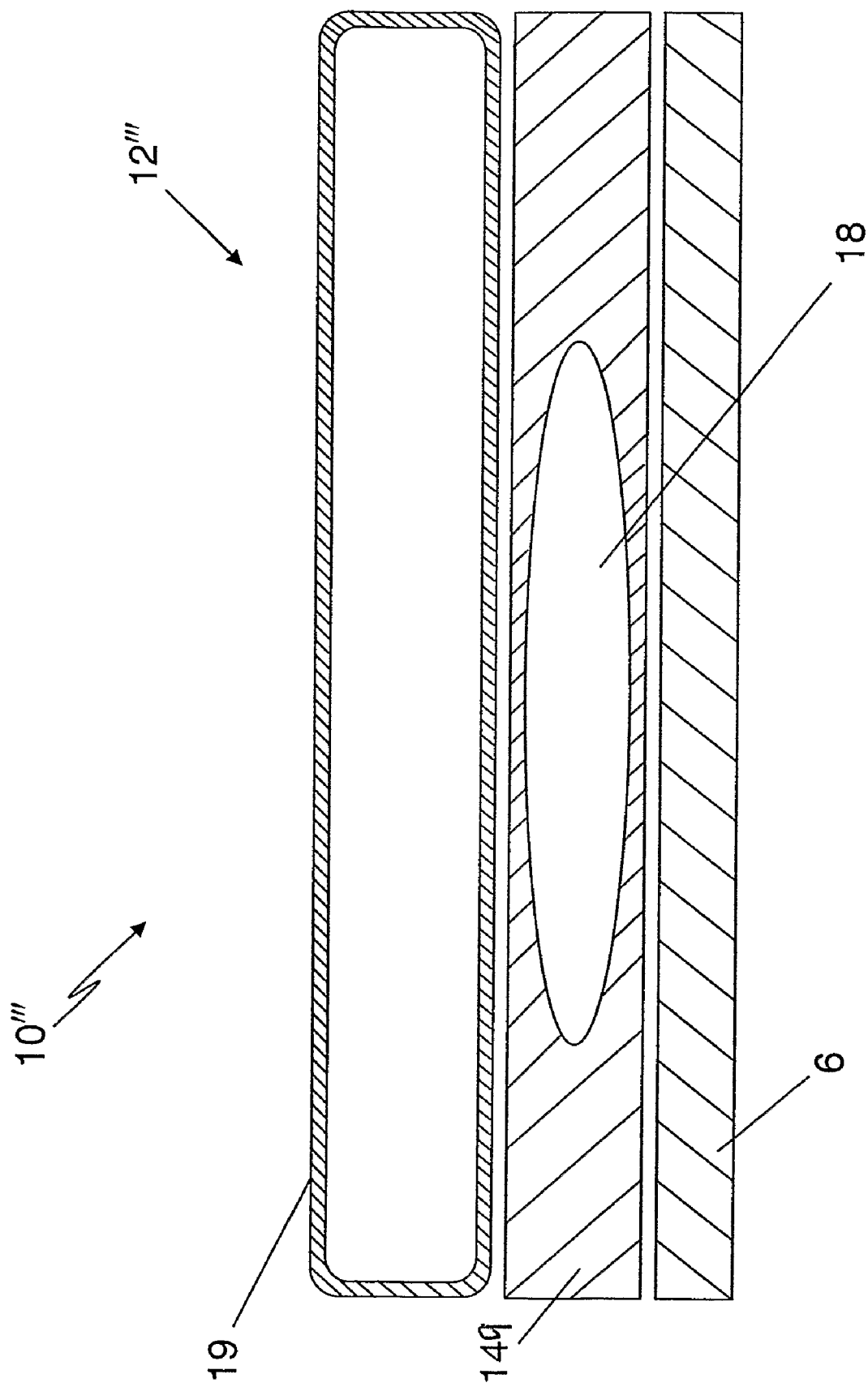
FIG. 5 is a cross-sectional view, in partial schematic, similar to FIG. 3, of another embodiment of a mattress assembly.

In yet another embodiment of mattress assembly 10''' as shown in FIG. 5, base support 149 includes a seat force sensor 18 which is positioned within the base support 149. Collector plate 16 (not shown) could also be positioned inside base support 149 above seat force sensor 18 in this embodiment. In addition to the embodiments described above, seat force sensor 18 may be removably coupled to existing mattresses or patient supports or incorporated in a fixed orientation into new patient supports.

Figure 6:
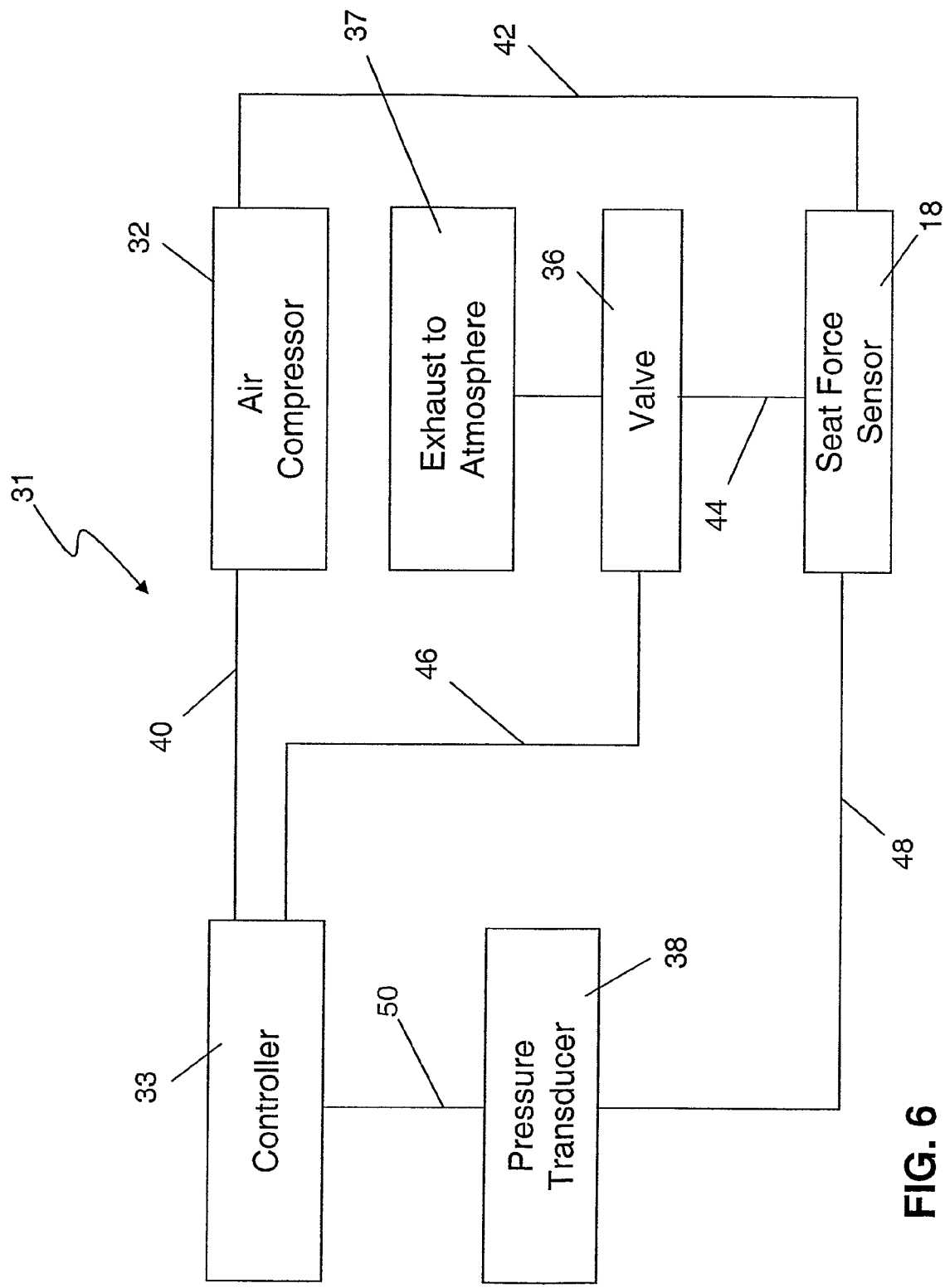
FIG. 6 is a block diagram of an illustrative embodiment of a patient weighing system.

Referring now to FIG. 6, a schematic of an illustrative embodiment operating system 31 including seat force sensor 18 is shown. A controller 33 is coupled to an air source, such as an air compressor 32, by signal line 40. If mattress assembly 10 is equipped with air compressor 32 configured to inflate the mattress 12, then such an air compressor 32 can also be used to inflate seat force sensor 18. Air compressor 32 is coupled to seat force sensor 18 by air line 42 which, in turn, is coupled to intake valve 36b. Intake valve 36b is coupled to intermediate air line 42 and air line 44 to prevent undesired leakage of air from seat force sensor 18 through compressor 32. Exhaust valve 36a is coupled to seat force sensor 18 by air line 44 and includes an exhaust to the atmosphere 37. Controller 33 is coupled to exhaust valve 36a by signal line 46a, and is in communication with intake valve 36b through signal line 46b. A pressure transducer 38 is coupled to seat force sensor 18 by air line 48. Pressure transducer 38 is also coupled to controller 33 by signal line 50. A conventional flow restrictor (not shown) may be used as a flow control for the output of the air compressor 32.

One illustrative method of operating the system 31 to determine the approximate patient weight is based upon measuring the change in the pressure in seat force sensor 18 when it has been inflated with a known amount of air. For this method, the same amount of air is placed in seat force sensor 18 for all patients positioned on mattress assembly 10. The pressure of the bladder of seat force sensor 18 can then be measured and correlated with an experimentally determined look-up table. For example, a pressure of 20 psi in seat force sensor 18 might correlate with a patient weighing 200 lbs., while a pressure of 17 psi might correlate with a patient weighing 180 lbs. Since the same amount of air is present in seat force sensor 18 for all patients, a higher pressure in seat force sensor 18 indicates a patient is heavier than a patient who creates a lower pressure in seat force sensor 18.

For the first step of this method, the bladder of seat force sensor 18 is first deflated or vented to atmosphere so the amount of air initially in the seat force sensor 18 is negligible. Next, a known volume of air is used to inflate the bladder of seat force sensor 18. This can be accomplished using air compressor 32 that outputs air at a known volumetric flow rate. The air compressor 32 is activated for a predetermined amount of time. In this method, the same amount of air is present in the seat force sensor 18 for each evaluation.

Figure 7:
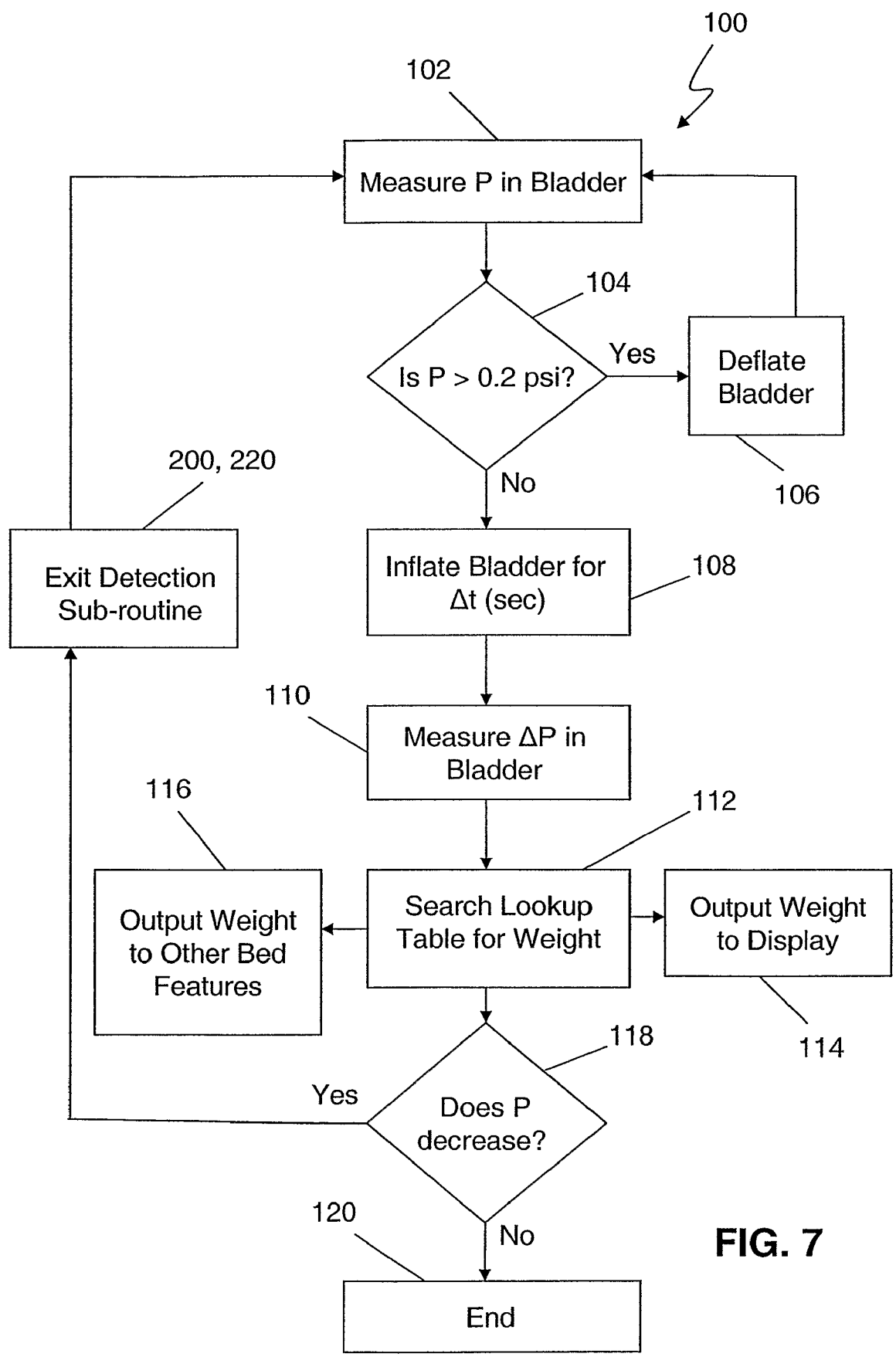
FIG. 7 is a flow chart showing an illustrative method of weighing a patient.

A flow chart 100 illustrating the steps of the illustrative method is shown in FIG. 7. To determine the patient's weight, seat force sensor 18 is positioned below the patient's sacral region in one of the manners detailed above. Pressure transducer 38 then measures the pressure in seat force sensor 18 and outputs a signal indicating the pressure to controller 33, as shown by step 102. Referring now to step 104, if the pressure in seat force sensor 18 is above a predefined pressure, for example, 0.2 psi, then controller 33 outputs a signal to valve 36a to deflate seat force sensor 18 until the pressure in seat force sensor 18 is below 0.2 psi, as shown by step 106. When the pressure in seat force sensor 18 is below the predetermined pressure, controller 30 sends a signal to valve 36a to close so that seat force sensor 18 can be inflated, as shown by step 108. Next, controller 33 actuates air compressor 32 to supply air to seat force sensor 18 for a predetermined amount of time, for example, 5 seconds, again as shown by step 108. It should be appreciated that other time intervals could be used and that the amount of time during which the air compressor 32 is activated determines the volume of air contained within the seat force sensor 18. After the air compressor has been active for the predetermined amount of time, and shuts down, pressure transducer 38 measures the pressure in seat force sensor 18 and outputs a signal indicative of the pressure to controller 33, as shown by step 110.

Figure 8:
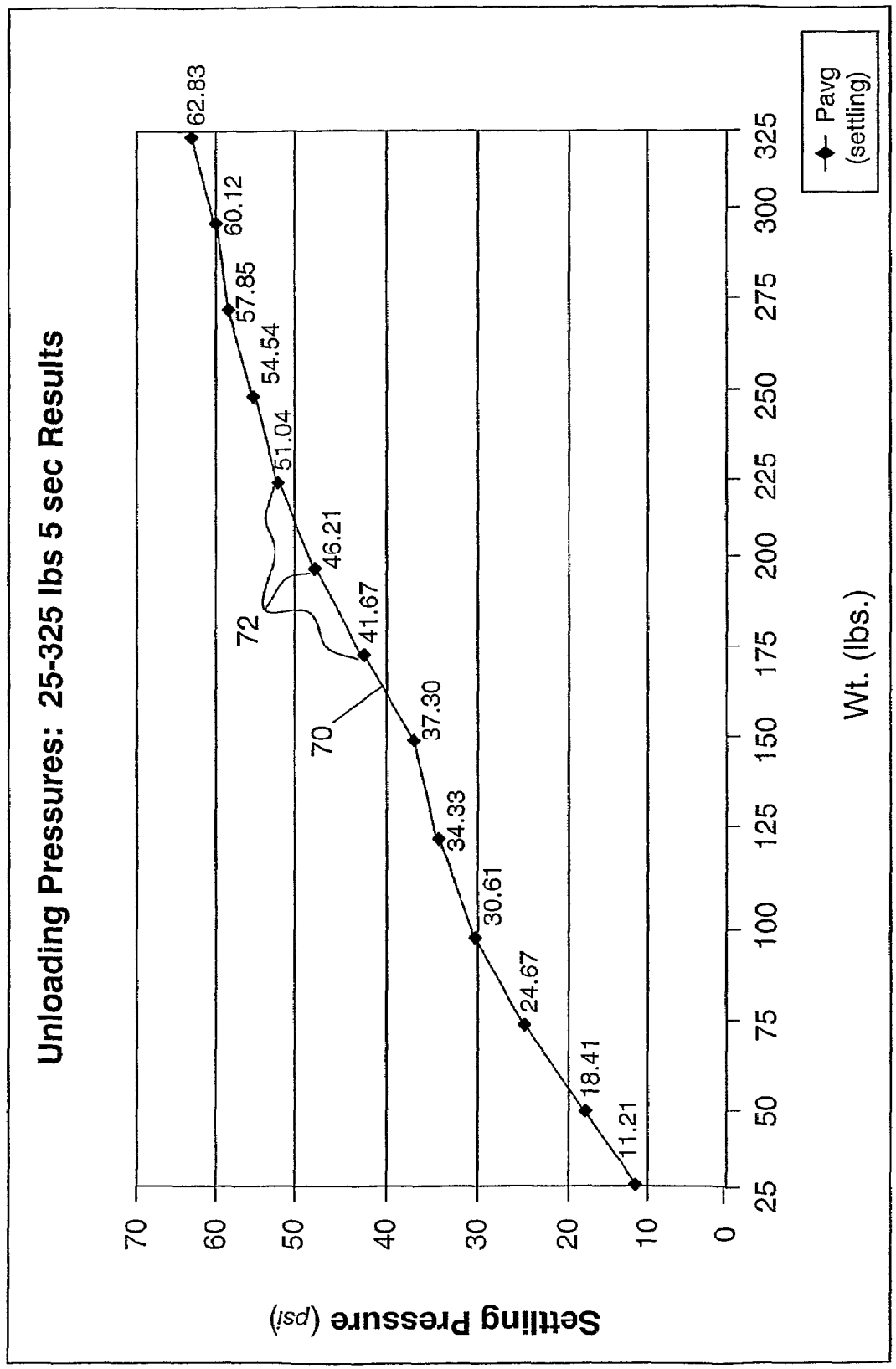
FIG. 8 is an illustrative chart of pressure versus pounds used for correlating the internal pressure of a seat force sensor with the approximate patient weight.

Referring now to step 112, controller 33 then correlates the pressure indicated by seat force sensor 18 with an approximate patient weight by using a lookup chart or table, such as that shown in FIG. 8, or by using a predetermined series of mathematical equations or algorithms. The controller 33 then outputs the approximate patient weight to a display, as shown in step 114, and/or outputs the data to other bed features, such as a mattress air controller for an inflatable bladder 19 in fluid mattress 12, as shown by step 116. For example, as explained below, the mattress air controller can then use the patient weight data to select an appropriate pressure setting for fluid mattress 12. Other bed functions, such as a heel pressure relief air bladder and patient turn assist air bladders, may also use the patient weight data to make adjustments to their respective settings. More particularly, the patient weight data may be used to determine proper pressure settings for the heel pressure relief air bladder and the turn assist air bladders.

Referring further to FIG. 8, a chart indicating an approximate patient weight compared to the pressure in seat force sensor 18 is shown. Line 70 connecting data set 72 represent experimental values that have been determined based upon the air compressor 32 being activated for 5 second predetermined time periods. As noted above, other suitable time periods could be used.

Patients of different sizes require different pressure settings when positioned on inflatable mattresses to prevent pressure ulcers. One method of setting the appropriate pressure setting for an inflatable mattress 12 is for a healthcare provider to approximate or guess the patient's weight or reference the patient's last recorded weight and input this data into a controller which then adjusts the pressure in the inflatable mattress 12 for a patient of that weight based on a lookup table. According to the present invention, the optimum pressure setting for the inflatable mattress 12 may be determined automatically when a patient enters the bed 2 by determining the patient weight using the seat force sensor 18. As represented by step 116 in FIG. 7, inflatable mattress 12 can receive the patient weight data directly from controller 33 so the proper pressure setting may be selected.

The controller 33 also looks for a pressure change within the seat force sensor 18 at decision step 118. Upon detection of such a pressure change, an exit detection sub-routine is initiated at block 200, as detailed below. If no pressure change is detected at step 118, then the process continues at block 120 where the controller 33 controls valves 36a and 36b to hold air pressure in the seat force sensor 18. The pressure in the seat force sensor 18 is measured and the process then returns to decision step 118.

Figure 9:
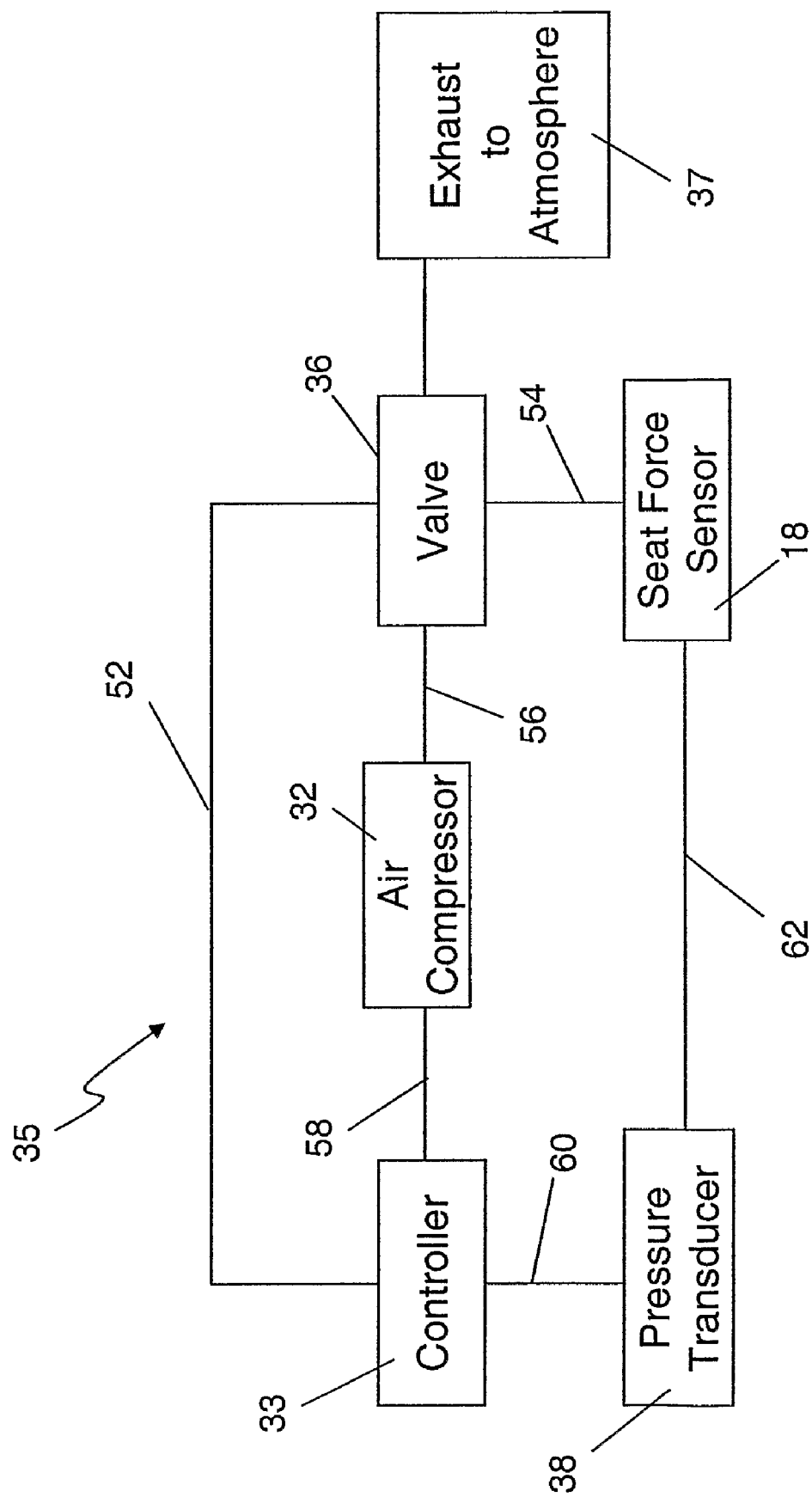
FIG. 9 is a block diagram of a further illustrative embodiment of a patient weighing system.

Referring now to FIG. 9, a schematic of an alternative embodiment operating system 35 is shown. In system schematic 35, controller 33 is coupled to valve 36 by signal line 52 and to air compressor 32 by signal line 58. Air compressor 32 is coupled to valve 36 by air line 56. Pressure transducer 38 is coupled to seat force sensor 18 by air line 62. Controller 33 is also coupled to pressure transducer 38 by signal line 60. Valve 36 is coupled to seat force sensor 18 by air line 54. Valve 36 includes an exhaust to atmosphere 37. In this illustrative embodiment, valve 36 receives air directly from air compressor 32 and controls air flow therefrom to seat force sensor 18, rather than air compressor 32 being directly connected to seat force sensor 18, as shown in the previous embodiment of FIG. 6.

To determine the approximate patient weight in connection with the system 35 of FIG. 9, the method illustrated in FIG. 7 is used with the exception of step 108. More particularly, an alternative step 108 is utilized in connection with system 35. When controller 33 actuates air compressor 32 to activate for a predetermined amount of time, controller 33 also actuates valve 36 to allow air to pass from air compressor 32 to seat force sensor 18. The remaining steps of the method, shown in FIG. 7, are substantially as described previously.

Figure 10:
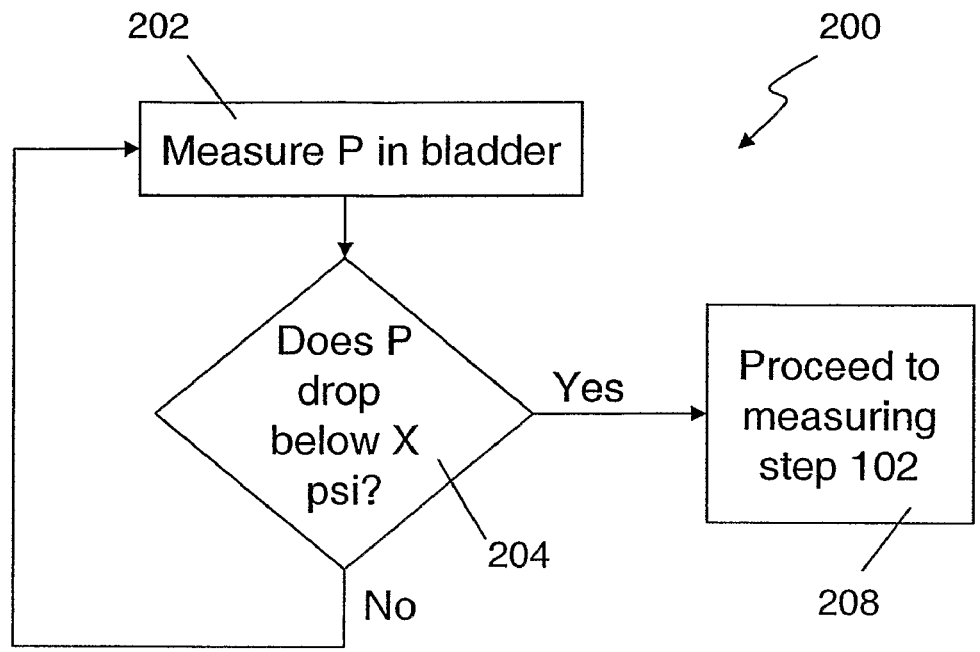
FIG. 10 is a flow chart showing another illustrative method of weighing a patient.

Referring now to FIG. 10, associated with the systems 31 and 35 of the present invention is a method for detecting when a patient has exited the mattress 12 or when the patient or a different patient enters or exits mattress 12. Referring back to FIG. 7, reevaluation of seat force, as shown by step 118, occurs when a pressure change is detected in the seat force sensor 18, for example, due to a patient's change of status such as exiting, entering, or repositioning in the bed. Referring to FIGS. 6 and 7, controller 33 monitors the pressure in seat force sensor 18 by receiving input from the pressure transducer 38.

In one illustrative embodiment, as shown in FIG. 10, method 200 may be considered a subroutine or subprocess which is activated after step 118 of method 100 in FIG. 7, if the pressure changes in seat force sensor 18. Method 200 includes the step of measuring the pressure (P) in the seat force sensor 18 in step 202. If the pressure in seat force sensor 18 drops below a predetermined level (X1) or rises above a predetermined level (X2) as shown by step 204, the process 200 returns to measuring step 102 of FIG. 7, as shown by block 208. If not, the pressure in the seat force sensor 18 is again monitored for change.

Figure 11:
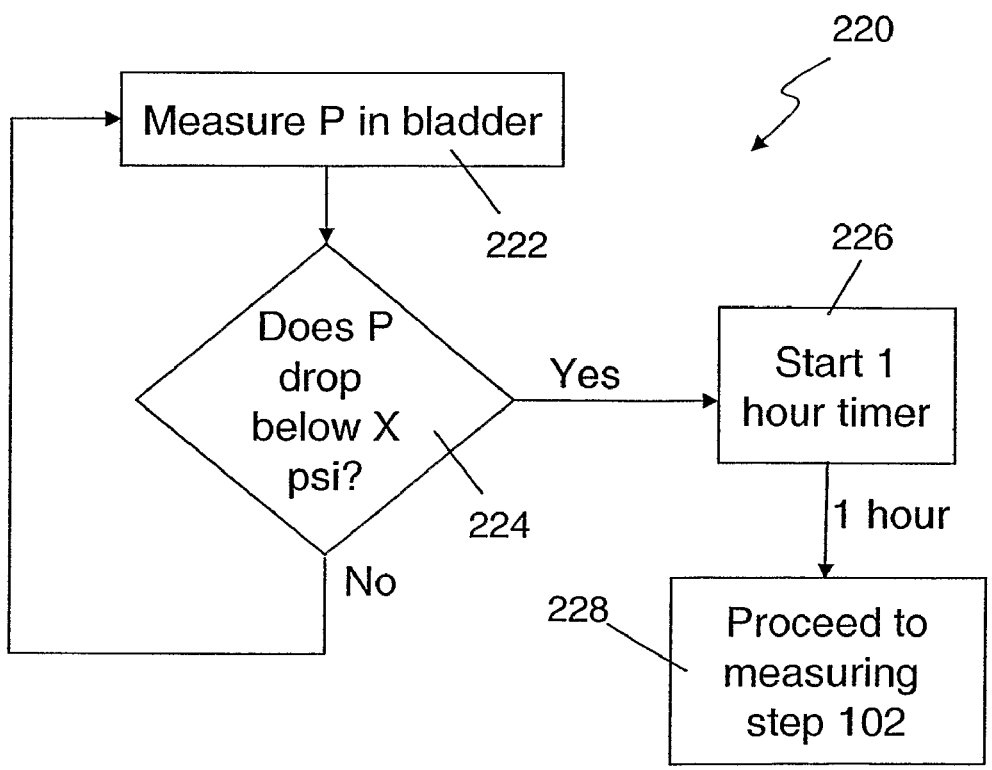
FIG. 11 is a flow chart showing a further illustrative embodiment of weighing a patient.

In another illustrative embodiment, shown in FIG. 11, method 220 is similar to method 200 in that it also monitors the pressure in the bladder at step 222. If the pressure drops to less than a predetermined level of pressure (X1) or rises above a predetermined level (X2) in step 224, a one hour timer activates in step 226 and returns to the measuring step 102 of FIG. 7 after the hour has passed, as shown by step 228. As will be appreciated by those of ordinary skill in the art, any suitable time period may be used. If mattress assembly 10 includes an inflatable mattress 12, this method assumes that pressure ulcers will not form on the patient within a one hour time period if a new patient has entered mattress assembly 10 and the pressure in the air mattress 12 is not correctly set for the new patient. The one hour time period can be adjusted based on the patient's specific needs.

Other methods of correlating the approximate patient weight with data from the seat force sensor 18 may be used. For example, the seat force sensor 18 could be inflated to a predetermined pressure and then inflated or deflated to a predetermined pressure while the time period of inflation or deflation is measured. The change in time could then be used to correlate with the approximate patient weight. Another method may include the steps of measuring an initial pressure of the seat force sensor 18 and activating the air compressor 32 to inflate or deflate the air bladder of the seat force sensor 18 until a predetermined volume of the air bladder is achieved. The amount of time or the change in pressure could then be used to correlate with the approximate patient weight. To use this method, the volume metric flow rate of the air compressor 32 would be required. If the amount of air flow out of the air compressor 32 is not predictable or is difficult to determine, the flow can be measured with a flow meter/transducer.

Figure 12:
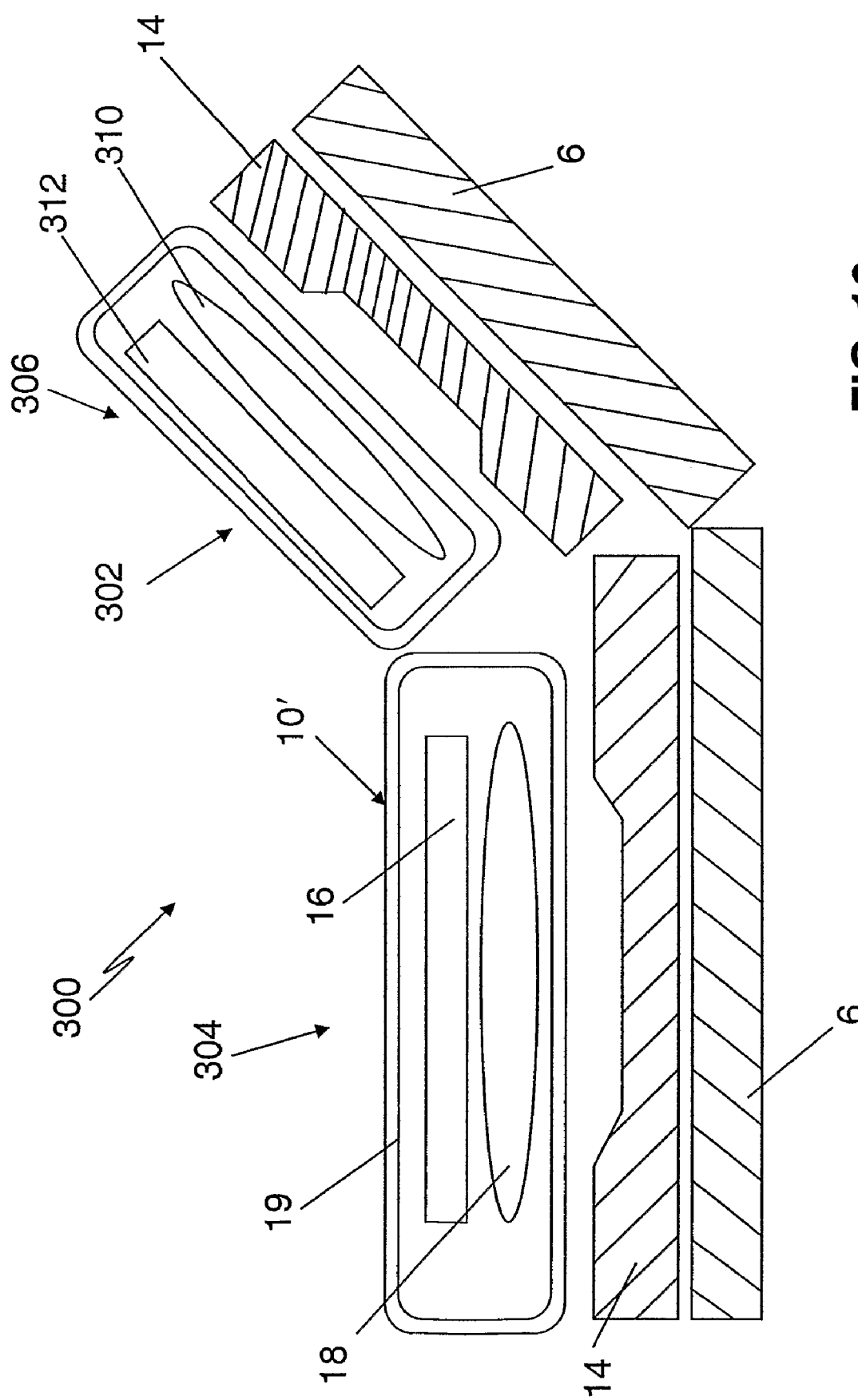
FIG. 12 is a cross-sectional view, in partial schematic, of another embodiment of a patient support assembly.

In a further illustrative embodiment of the present invention shown in FIG. 12, an adjustable patient support 300 is shown. Patient support 300 includes at least a head section 302 and a seat section 304. Head section 302 can be elevated to raise a patient positioned on patient support 300 to a sitting position. In this embodiment, mattress assembly 109 is placed on seat section 304 and a second mattress assembly 306 is placed on head section 302. Mattress assembly 306 is identical to mattress assembly 109, except that it is positioned on head section 304. Mattress assembly 306 includes a back force sensor 310 and may include a collector plate 312. The back force sensor 310 is substantially identical to the seat force sensor 18, while the collector plate 312 is substantially identical to the collector plate 16. More particularly, the method of operation for back force sensor 310 is the same method used to operate seat force sensor 18. Utilizing back force sensor 310 and seat force sensor 18 allows a patient positioned on patient support 300 to be weighed even when head section 302 is elevated as illustrated in FIG. 12. A controller can compare the pressures in seat force sensor 18 and back force sensor 310 to a look-up table to determine the patient's weight. Alternatively, the values from the seat force sensor 18 and back force sensor 310 may be used in algorithms to determine the patient's weight and position.

It should be noted that the change of pressure detected by the seat force sensor 18 of the previous illustrated embodiments may be replaced with a change of pressure detected by the back force sensor 310 to trigger a measurement cycle.

Figure 13:
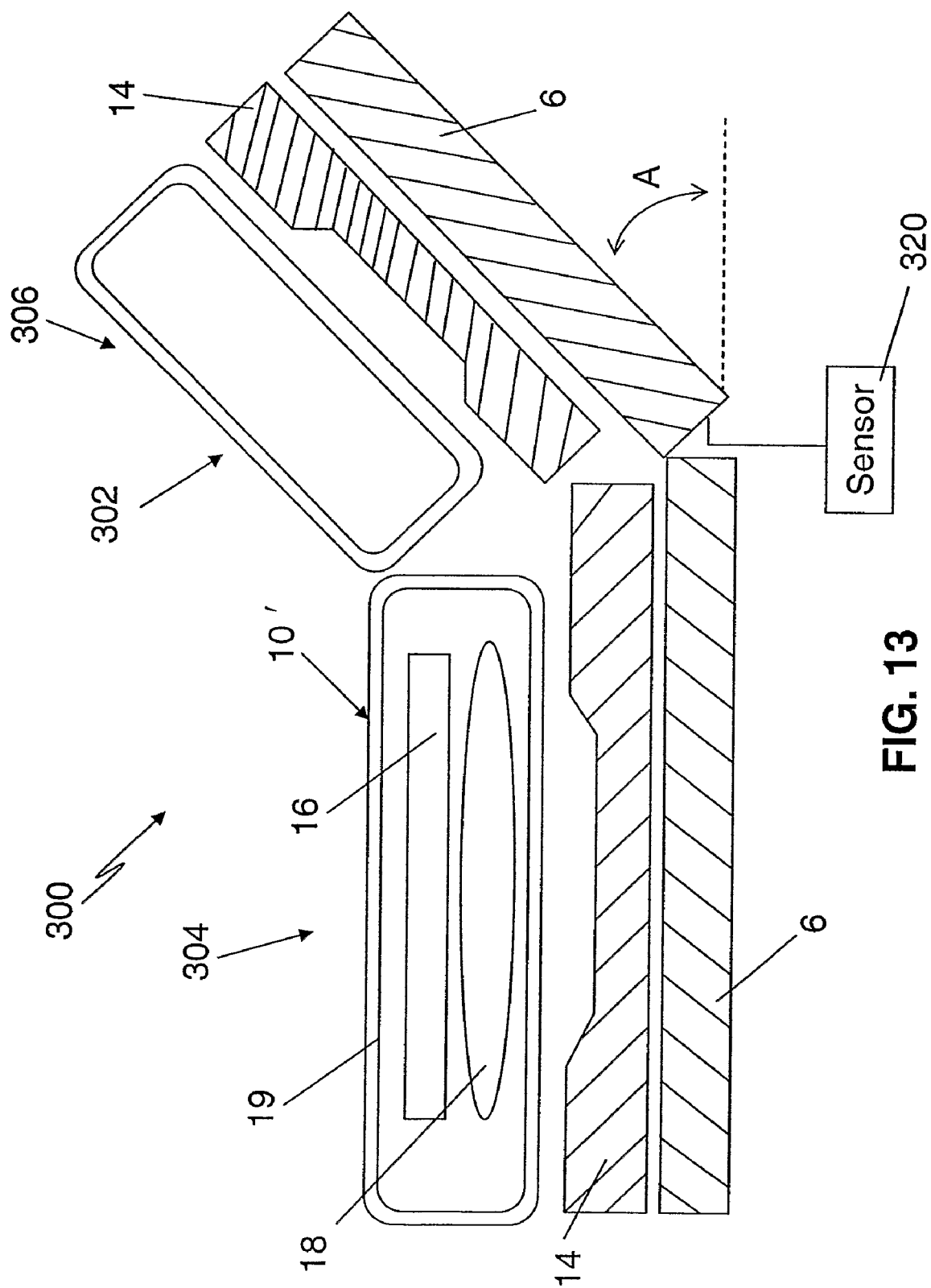
FIG. 13 is a cross-sectional view, in partial schematic, of another embodiment of a patient support assembly.

In an alternative embodiment of FIG. 12, back force sensor 310 and collector plate 312 are not present in mattress assembly 306. Angle sensor 320 is coupled to patient support 300 as shown in FIG. 13 to determine the angle A of inclination or declination of head section 302 relative to seat section 304 and output a signal indicative of the angle A to a controller. The controller then compares the angle A and the pressure in seat force sensor 18 to a look-up table to determine the approximate patient weight. Again, an algorithm may be substituted for the look-up table. The weight of a patient positioned on patient support 300 can be determined even if head section 302 is inclined or declined relative to seat section 304.

It should be noted that a seat force sensor 18 (FIGS. 12 and 13) may be used in combination with a back force sensor 310 (FIG. 12) and an angle sensor 320 (FIG. 13) to determine a patient weight distribution having improved accuracy (i.e. detection of a patient sitting up).

Figure 14:
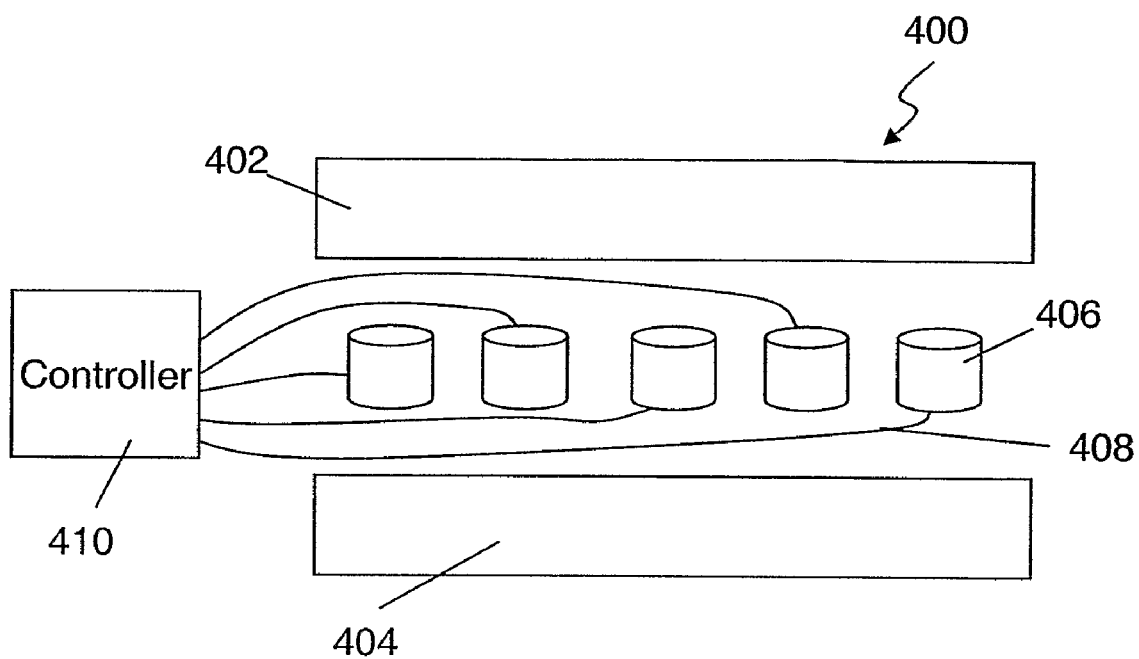
FIG. 14 is a partially exploded side elevational view, in partial schematic, of another embodiment of a weight sensor of the present invention.

Another embodiment of seat force sensor 18 is shown in FIG. 14. Seat force sensor 400 includes an upper plate 402, a lower plate 404, a plurality of weight sensors 406, wires 408, and a controller 410. Upper plate 402 and lower plate 404 are similar to collector plate 16 and are also used to concentrate the patient's weight uniformly on the weight sensors 406. Both plates 402 and 404 are illustratively made of metal, plastic, wood, or any other suitable rigid or semi-rigid material. Plates 402 and 404 are sized to support the patient's sacral or seat region.

Weight sensors 406 are positioned between plates 402 and 404 and produce an electrical signal that is proportional to the force applied to them. Weight sensors 406 may include force transducers such as force sensing resistor pads, load cells, resistive ink-type transducers such as FLEXIFORCE by TEKSCAN, or any other suitable force transducer. Any number of weight sensors may be used in seat force sensor 400. If more weight sensors 406 are used in seat force sensor 400, smaller load cells having better accuracy can be used which could improve the overall accuracy of seat force sensor 400. If a smaller number of load cells are used the capacity of each load cell must be greater and as a result, the accuracy of each load cell is lower which lowers the overall accuracy of seat force sensor 400.

The plurality of weight sensors 406 are connected to controller 410 by wires 408. In the illustrated embodiment five weight sensors are used. Seat force sensors configured to weigh larger patients may require more weight sensors 406. Controller 410 receives the electrical signals via wires 408 from each weight sensor 406. Controller 410 then correlates the signals received from weight sensor 406 with an approximate patient weight by using a look-up chart or table similar to that shown in FIG. 8 or by using a predetermined series of mathematical equations or algorithms. Controller 410 then outputs the approximate patient weight to a display and/or outputs the data to other bed features, such as a mattress air controller for an inflatable bladder in a fluid mattress. As explained above, the mattress air controller can then use the patient weight data to select an appropriate pressure setting for a fluid mattress. Other bed functions, such as a heel pressure relief air bladder and patient turn assist air bladders, may also use the patient weight data to make adjustments to their respective settings.

Figure 15:
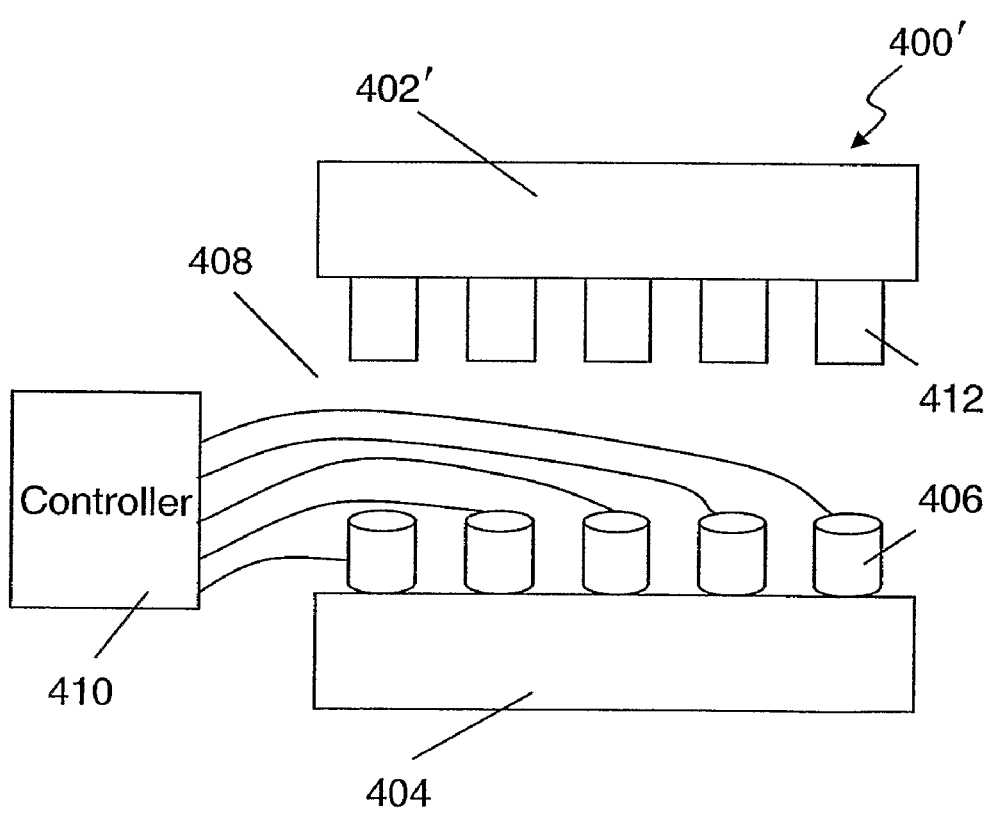
FIG. 15 is a partially exploded side elevational view, in partial schematic, of a further illustrative embodiment of a weight sensor of the present invention.

Another embodiment of seat force sensor 4009 is shown in FIG. 15. Seat force sensor 4009 is similar to seat force sensor 400 with the exception of upper plate 4029 and standoffs 412. Upper plate 4029 includes a plurality of standoffs 412, each positioned directly over one of the plurality of weight sensors 406, which are mounted on lower plate 404. Seat force sensor 4009 includes a standoff 412 for each corresponding weight sensor 406. Standoffs 412 focus the weight of the patient on the weight sensors 406 to provide a more accurate patient weight. The electrical signals from the weight sensors 406 are carried to controller 410 through wires 408. Any number of weight sensors 406 and standoffs 412 could be used in seat force sensor 4009. For illustration, five weight sensors 406 are shown in FIG. 15.

Figure 16:
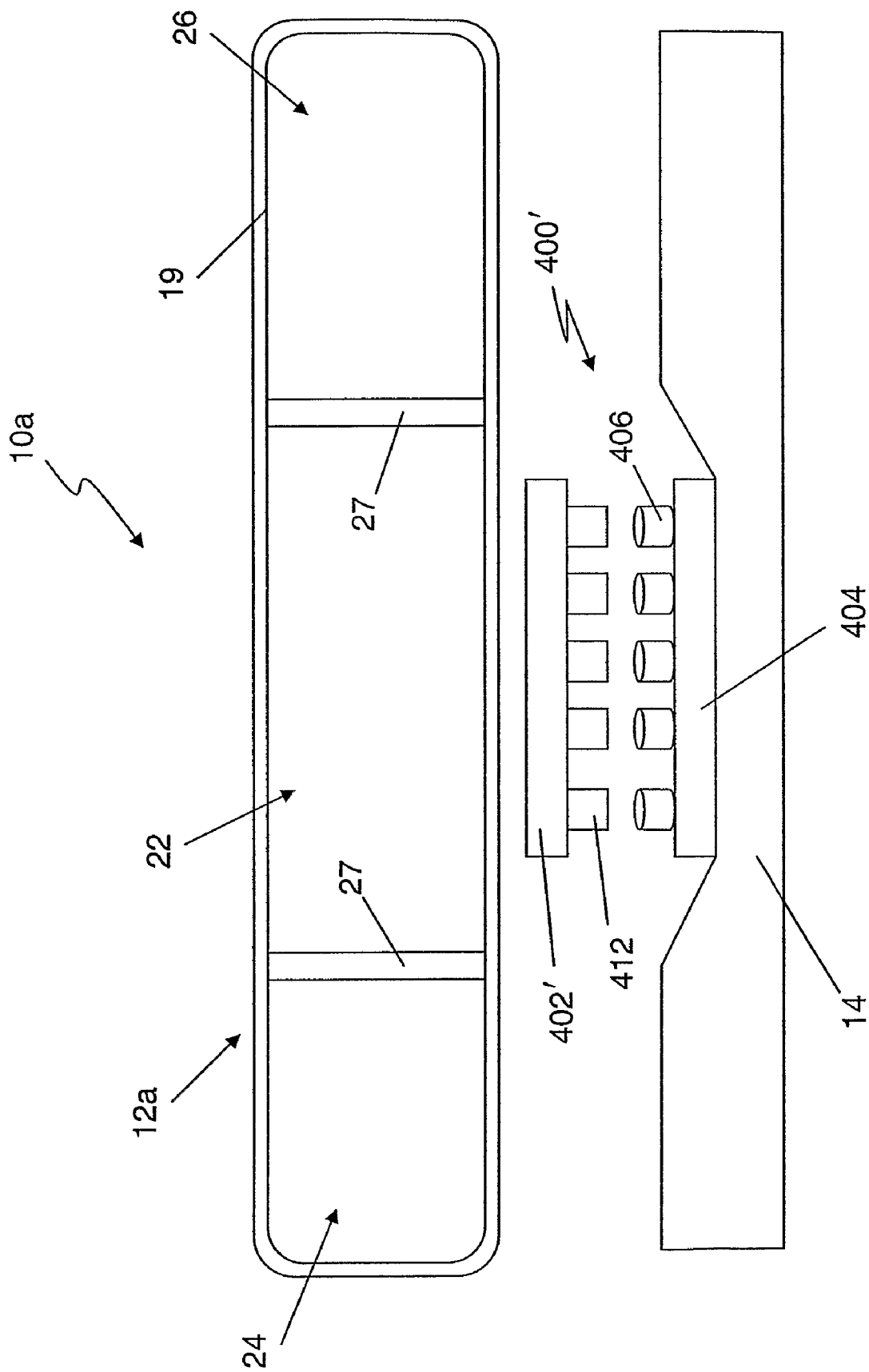
FIG. 16 is a partially exploded side elevational view, in partial schematic, of an illustrative embodiment of a mattress assembly including the weight sensor shown in FIG. 15.

As shown in FIG. 16, seat force sensor 4009 is illustratively positioned in the same orientation as seat force sensor 18, shown in FIG. 2. Upper plate 4029 is configured to substantially support a patient's entire seat region and to substantially focus and uniformly apply the patient's weight to seat force sensor 4009. As discussed above, upper plate 4029 is similar to collector plate 16 and is configured to focus the force of the patient's weight uniformly upon standoffs 412, which in turn apply pressure to weight sensors 406. When the patient is positioned on mattress assembly 10a, upper plate 4029 is depressed which causes standoffs 412 to apply pressure to weight sensors 406 to generate electrical signals proportional to the force applied to them. Controller 410 (not shown) receives the electrical signals and correlates them to an approximate patient weight and outputs the patient weight to a display and/or other bed features such as a heel pressure relief system or a patient turn assist system.

Figure 17:
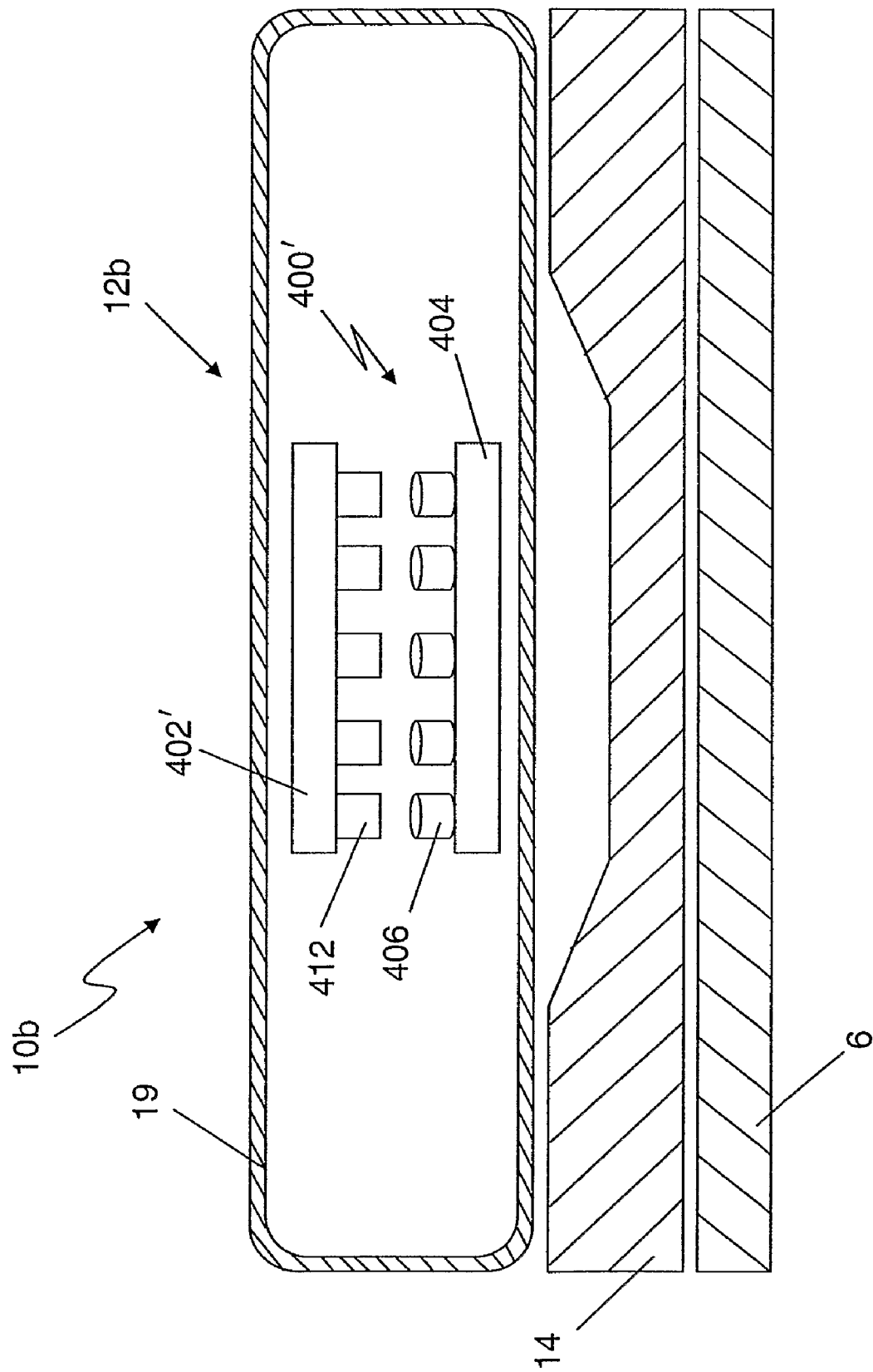
FIG. 17 is a cross-sectional view, in partial schematic, of another embodiment of a mattress assembly including the weight sensor shown in FIG. 15.

Referring now to FIG. 17, a further illustrative mattress assembly 10b similar to mattress assembly 109, shown in FIG. 3, is shown. Fluid mattress or support 12b is shown positioned on base support 14 of mattress assembly 10b. In this embodiment, fluid mattress 12b of mattress assembly 10b includes seat force sensor 4009. Seat force sensor 4009 is positioned within air bladder 19 of fluid mattress 12b. More particularly, seat force sensor 4009 is positioned below the patient's sacral or seat region while positioned within air bladder 19 of fluid mattress 12b.

Figure 18:
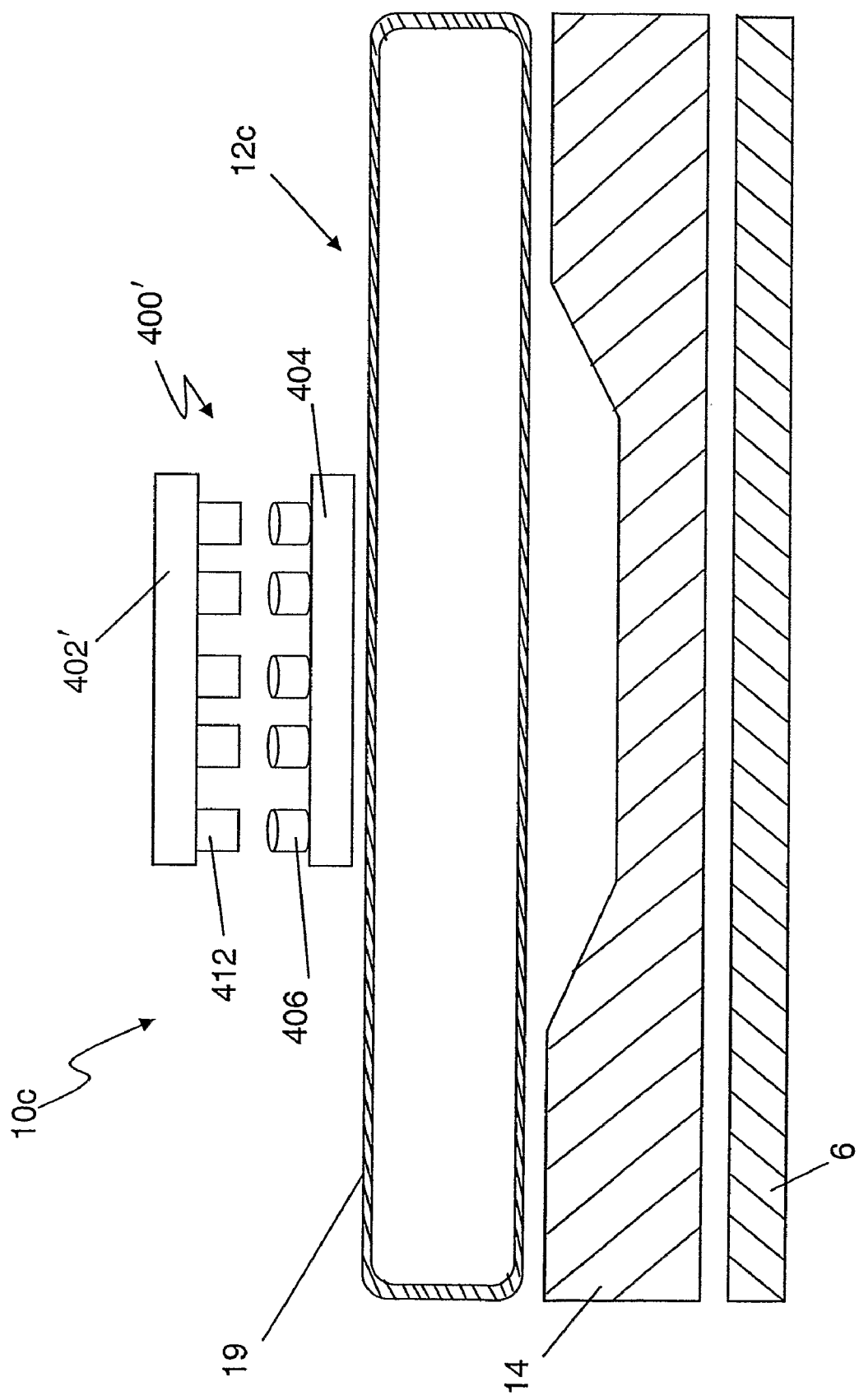
FIG. 18 is a cross-sectional view, in partial schematic, of another embodiment of a mattress assembly including the weight sensor shown in FIG. 15.

In another embodiment of mattress assembly 10c, as shown in FIG. 18, seat force sensor 4009 is positioned on top of fluid mattress 12c similar to the embodiment shown in FIG. 4. In this position, seat force sensor 4009 is directly beneath a patient positioned on mattress assembly 10c. The patient's sacral region contacts upper plate 4029 and forces standoffs 412 downward applying pressure to weight sensors 406.

Figure 19:
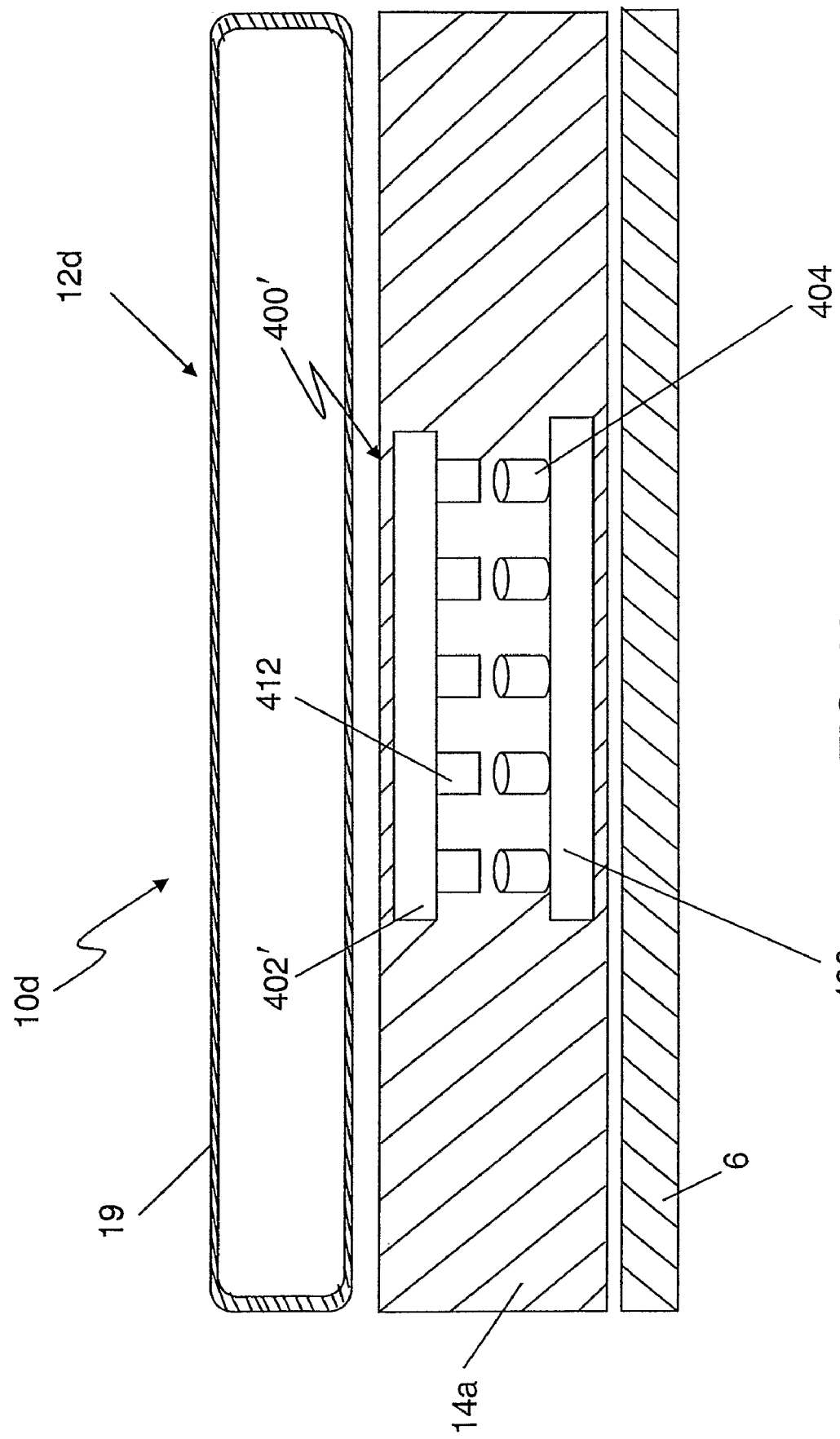
FIG. 19 is a cross-sectional view, in partial schematic, of another embodiment of a mattress assembly including the weight sensor shown in FIG. 15.

In yet another embodiment of mattress assembly 10d, as shown in FIG. 19, base support 14a includes a seat force sensor 4009 which is positioned within the base support 14a which is supported by frame 6. In addition to the embodiments described above, seat force sensor 400 may be removably coupled to existing mattresses or patient supports or incorporated in a fixed orientation into new patient supports.

Figure 20:
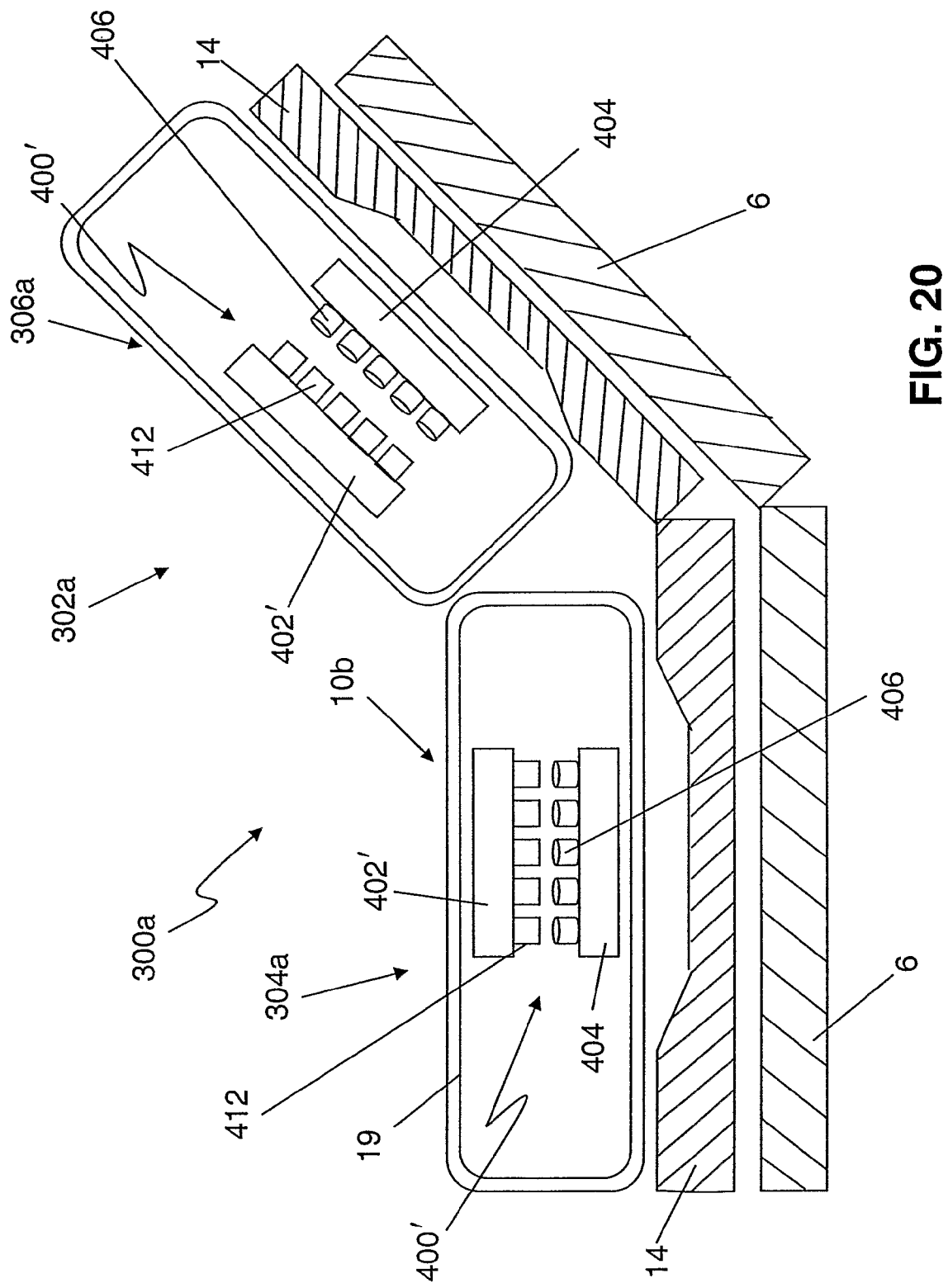
FIG. 20 is a cross-sectional view, in partial schematic, of another embodiment of a patient support assembly including weight sensors similar to the one shown in FIG. 15.

In a further illustrative embodiment of the present invention shown in FIG. 20, an adjustable patient support 300a is shown. Patient support 300a is similar to patient support 300 shown in FIG. 12. Seat force sensors 18 have been replaced by seat force sensors 4009. Patient support 300a includes at least a head section 302a and a seat section 304a. Head section 302a can be elevated to raise a patient position on patient support 300a to a sitting position. In this embodiment, mattress assembly 10b is placed on seat section 304a and a second mattress assembly 306a is placed on head section 302a. Mattress assembly 306a is identical to mattress 10b, except that it is positioned on head section 304a. Mattress assembly 306a includes a back force sensor 4009. Back force sensor 4009 is substantially identical to the seat force sensor 4009. More particularly, the method of operation of back force sensor 4009 is the same method used to operate seat force sensor 4009. Utilizing back force sensor 4009 and seat force sensor 4009 allows a patient positioned on patient support 300a to be weighed even when the head section 302a is elevated as illustrated in FIG. 20. A controller can compare the electrical signals received from weight sensors 406 of seat force sensor 4009 and back force sensor 4009 to a look-up table to determine the patient's weight or head angle. Alternatively, the electrical signals from seat force sensor 4009 and back force sensor 4009 may be used in algorithms to determine a patient's weight.

Figure 21:
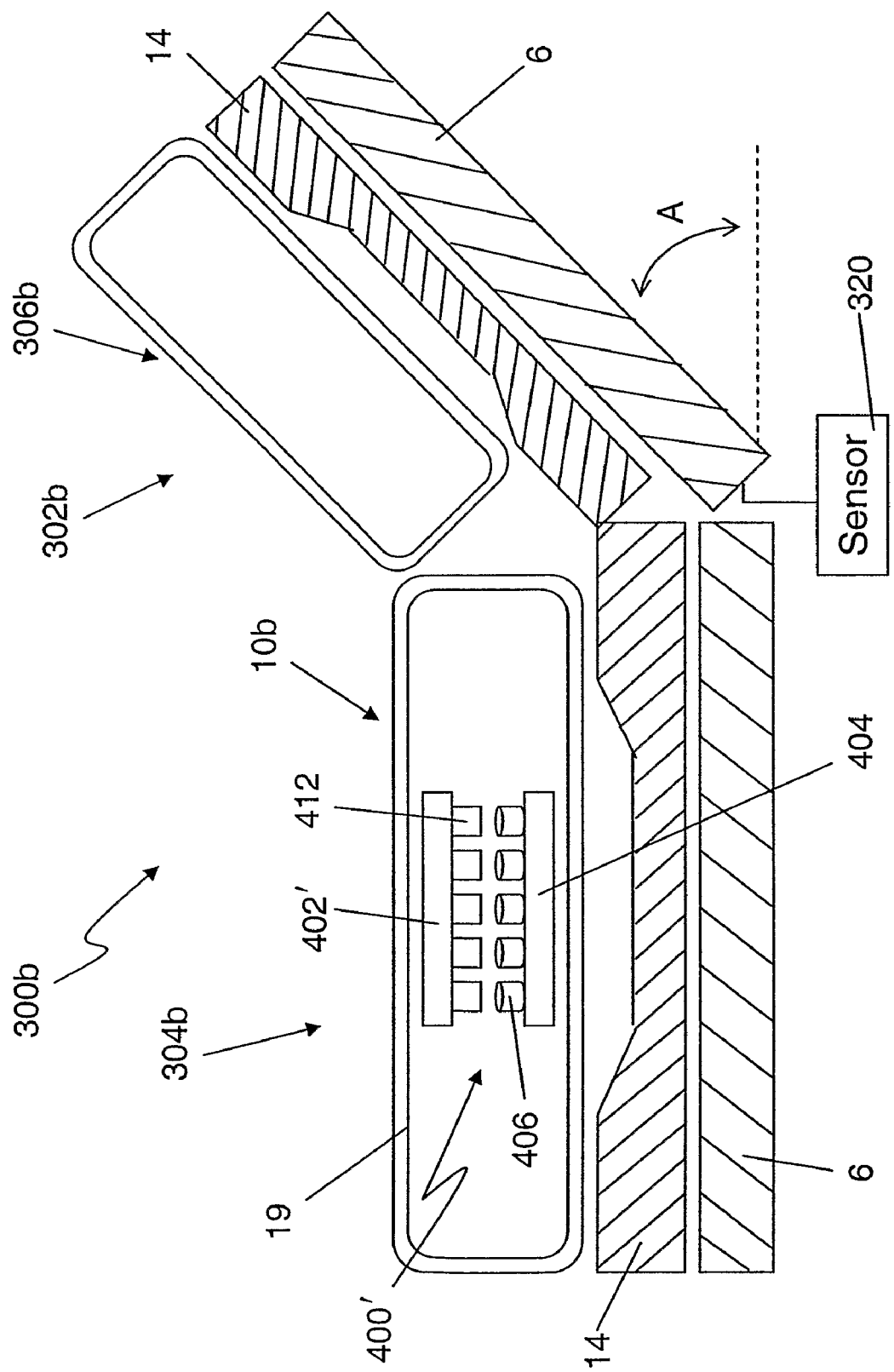
FIG. 21 is a cross-sectional view, in partial schematic, of another embodiment of a patient support assembly including the patient weight sensor shown in FIG. 15.

FIG. 21 illustrates another embodiment of FIGS. 13 and 20, wherein back force sensor 4009 is not present in mattress assembly 306b. Angle sensor 320 is coupled to patient support 300b as shown in FIG. 21 to determine the angle A of inclination or declination of head section 302b relative to seat section 304b. Sensor 320 outputs a signal indicative of the angle A to a controller. The controller then compares the angle A and the electrical signals received from seat force sensor 4009 to a look-up table to determine the approximate patient weight. Again, an algorithm may be substituted for the lookup table. The weight of the patient positioned on patient support 300b can be determined even if head section 302b is inclined or declined relative to seat section 304b.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

The invention claimed is:

1. A patient support comprising:
   a mattress having a head section, a foot section spaced from the head section, and a seat section between the head section and the foot section, the seat section being dimensioned to support a seat region of a person,
   an inflatable cell associated with the seat section,
   an air source operable to inflate the inflatable cell,
   a pressure sensor operable to measure pressure in the inflatable cell,
   a substantially rigid collector plate located above the inflatable cell and arranged to uniformly concentrate a portion of a person's weight on the inflatable bladder, and
   a controller operably coupled to the pressure sensor and to the air source, the controller being operable to automatically determine a value for total body weight of a person positioned on the mattress based on an output of the pressure sensor.

2. The patient support of claim 1, comprising at least one baffle in the inflatable cell.

3. The patient support of claim 1, wherein the mattress includes a plurality of inflatable bladders and the controller is configured to signal the air source to adjust the pressure of at least one of the mattress bladders based upon the value for the total body weight as determined by the controller from the output of the pressure sensor.

4. The patient support of claim 1, further comprising a second inflatable cell associated with the head section of the mattress and a second pressure sensor operable to measure pressure in the second inflatable cell, wherein the controller is operably coupled to the second pressure sensor and is operable to determine the value for the total body weight of a person positioned on the mattress based on output signal outputs from the first and second pressure sensors.

5. The patient support of claim 4, further comprising an angle sensor coupled to the head section of the mattress to output a signal indicative of the angle of inclination of the head section relative to the seat section, wherein the controller is operable to determine the value for the total body weight of a person positioned on the mattress based on the outputs from the first and second pressure sensors and the angle sensor output signal.

6. The patient support of claim 1, further comprising an angle sensor coupled to the head section of the mattress to output a signal indicative of the angle of inclination of the head section relative to the seat section, wherein the controller is operable to determine the value for the total body weight of a person positioned on the mattress based on the output from the pressure sensor and the angle sensor output signal.

7. A patient support comprising:
   a mattress having a head section, a foot section spaced from the head section, and a seat section between the head section and the foot section, the seat section being dimensioned to support a seat region of a person, at least the foot section including at least one inflatable bladder,
   an air source operable to inflate the at least one inflatable bladder,
   a force sensor sized to fit within the dimensions of the seat section of the mattress and configured to output a signal indicative of force applied to the seat section of the mattress, the force sensor comprising a substantially rigid lower plate, a plurality of force transducers above the lower plate, and a substantially rigid upper plate configured to concentrate a portion of a person's weight on the plurality of force transducers thereby to produce the signal, and
   a controller configured to receive the output signal from the force sensor and automatically signal the air source to adjust pressure in the foot section of the mattress based on the output of the force sensor.

8. The patient support of claim 7, further comprising a heel pressure relief bladder and wherein the controller is configured to signal the air source to adjust pressure in the heel pressure relief air bladder based on the output of the seat section force sensor.

9. The patient support of claim 7, wherein the plurality of force transducers of the force sensor comprises a plurality of force sensing resistor pads.

10. The patient support of claim 9, wherein the upper plate positioned above the plurality of force transducers is substantially rigid and the lower plate positioned below the plurality of force transducers is substantially rigid.

11. The patient support of claim 10, wherein the lower plate includes a plurality of standoffs, each standoff being positioned directly over a corresponding one of the plurality of force transducers.

12. The patient support of claim 1, wherein the controller is operable to automatically determine the value for total body weight of a person by using a look up table.

13. The patient support of claim 1, wherein the controller is operable to automatically determine the value for total body weight of a person by using a mathematical equation.

14. The patient support of claim 1, wherein at least one of the head section, the seat section, and the foot section comprises a foam material.

15. The patient support of claim 1, wherein the inflatable cell is situated within the seat section.

16. The patient support of claim 4, wherein the inflatable cell is situated within the seat section.

17. The patient support of claim 16, wherein the second inflatable cell is situated within the head section.

18. The patient support of claim 1, wherein the inflatable cell is situated outside the mattress and adjacent the seat section.

19. The patient support of claim 7, wherein the plurality of force transducers of the force sensor comprises a plurality of a plurality of load cells.

20. The patient support of claim 7, wherein the plurality of force transducers of the force sensor each comprise resistive ink.

* * * * *